United States Patent
Schuster et al.

(10) Patent No.: US 11,452,995 B2
(45) Date of Patent: *Sep. 27, 2022

(54) CATALYST AND PROCESS FOR PREPARING DIMETHYL ETHER

(71) Applicant: BASF SE, Ludwigshafen am Rhein (DE)

(72) Inventors: Sabine Schuster, Ludwigshafen am Rhein (DE); Ekkehard Schwab, Ludwigshafen am Rhein (DE); Stefan Altwasser, Ludwigshafen am Rhein (DE); Harry Kaiser, Heidelberg (DE); Stephan A. Schunk, Heidelberg (DE); Manuela Gaab, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 100 days.

This patent is subject to a terminal disclaimer.

(21) Appl. No.: 16/956,677

(22) PCT Filed: Dec. 20, 2018

(86) PCT No.: PCT/EP2018/086090
§ 371 (c)(1),
(2) Date: Jun. 22, 2020

(87) PCT Pub. No.: WO2019/122075
PCT Pub. Date: Jun. 27, 2019

(65) Prior Publication Data
US 2020/0330965 A1    Oct. 22, 2020

(30) Foreign Application Priority Data

Dec. 20, 2017 (EP) .................... 17208929

(51) Int. Cl.

| | | |
|---|---|---|
| *B01J 29/06* | (2006.01) | |
| *B01J 29/46* | (2006.01) | |
| *C07C 41/09* | (2006.01) | |
| *B01J 29/072* | (2006.01) | |
| *B01J 29/40* | (2006.01) | |
| *B01J 29/42* | (2006.01) | |
| *B01J 37/00* | (2006.01) | |
| *B01J 27/14* | (2006.01) | |
| *B01J 35/02* | (2006.01) | |
| *B01J 21/06* | (2006.01) | |
| *B01J 35/00* | (2006.01) | |
| *B01J 23/20* | (2006.01) | |
| *B01J 23/72* | (2006.01) | |
| *B01J 21/08* | (2006.01) | |
| *C07C 43/04* | (2006.01) | |

(52) U.S. Cl.
CPC ............... *B01J 29/46* (2013.01); *B01J 21/06* (2013.01); *B01J 21/08* (2013.01); *B01J 23/20* (2013.01); *B01J 23/72* (2013.01); *B01J 27/14* (2013.01); *B01J 29/06* (2013.01); *B01J 29/072* (2013.01); *B01J 29/40* (2013.01); *B01J 29/42* (2013.01); *B01J 35/0006* (2013.01); *B01J 35/02* (2013.01); *B01J 35/023* (2013.01); *B01J 35/026* (2013.01); *B01J 37/0009* (2013.01); *C07C 41/09* (2013.01); *B01J 2229/42* (2013.01); *B01J 2523/00* (2013.01); *B01J 2523/17* (2013.01); *B01J 2523/31* (2013.01); *B01J 2523/48* (2013.01); *C07C 43/043* (2013.01); *C07C 2529/072* (2013.01); *C07C 2529/76* (2013.01); *Y02P 20/52* (2015.11); *Y02P 30/20* (2015.11)

(58) Field of Classification Search
CPC ........ B01J 2229/42; B01J 29/46; B01J 29/06; B01J 29/072; B01J 29/40; B01J 27/14; B01J 37/0009; B01J 35/0006; B01J 35/023; B01J 35/026; B01J 21/04; B01J 21/06; B01J 21/08; B01J 23/20; B01J 23/72; B01J 2523/00; B01J 2523/17; B01J 2523/31; B01J 2523/48; Y02P 20/52; Y02P 30/20; C07C 41/01; C07C 41/09; C07C 43/043; C07C 2529/76; C07C 2529/072
USPC .......... 502/63, 64, 66, 69, 71; 518/700, 702, 518/707; 568/698
See application file for complete search history.

(56) References Cited

U.S. PATENT DOCUMENTS

| | | | |
|---|---|---|---|
| 4,683,214 A | 7/1987 | Angevine et al. | |
| 6,579,347 B1 | 6/2003 | Wakita et al. | |
| 7,273,893 B2 * | 9/2007 | Yao | B01J 35/0006 518/713 |
| 2005/0143610 A1 | 6/2005 | Mitchell et al. | |
| 2011/0060169 A1 | 3/2011 | Kaizik et al. | |

(Continued)

FOREIGN PATENT DOCUMENTS

| | | |
|---|---|---|
| EP | 0845294 A2 | 6/1998 |
| EP | 1151790 A1 | 11/2001 |

(Continued)

OTHER PUBLICATIONS

International Preliminary Reporton Patentability received for PCT Patent Application No. PCT/EP2018/086090, dated Mar. 5, 2020, 15 pages.

(Continued)

*Primary Examiner* — Elizabeth D Wood
(74) *Attorney, Agent, or Firm* — Faegre Drinker Biddle & Reath LLP

(57) ABSTRACT

The invention relates to a catalyst and catalyst layer and process for preparing dimethyl ether from synthesis gas or methanol as well as the use of the catalyst or catalyst layer in this process.

14 Claims, No Drawings

(56) References Cited

U.S. PATENT DOCUMENTS

| | | |
|---|---|---|
| 2012/0065449 A1 | 3/2012 | Loewenstein et al. |
| 2012/0115966 A1* | 5/2012 | Fu ........................ B01J 23/8892 518/715 |
| 2014/0271446 A1 | 9/2014 | Desmedt et al. |
| 2016/0016153 A1 | 1/2016 | Dubois et al. |

FOREIGN PATENT DOCUMENTS

| | | |
|---|---|---|
| EP | 1238701 A1 | 9/2002 |
| WO | 2011/075278 A1 | 6/2011 |
| WO | 2013/120938 A1 | 8/2013 |
| WO | 2013/120945 A1 | 8/2013 |
| WO | 2013/160133 A1 | 10/2013 |
| WO | 2014/174107 A1 | 10/2014 |
| WO | WO/2016/187773 A1 | 12/2016 |

OTHER PUBLICATIONS

International Search Report and Written Opinion received for PCT Patent Application No. PCT/EP2018/086090, dated Apr. 2, 2019, 20 pages.

* cited by examiner

CATALYST AND PROCESS FOR PREPARING DIMETHYL ETHER

CROSS-REFERENCE TO RELATED APPLICATIONS

This application is a national stage application (under 35 U.S.C. § 371) of PCT/EP2018/086090, filed Dec. 20, 2018, which claims benefit of European Application No. 17208929.4, filed Dec. 20, 2017, both of which are incorporated herein by reference in their entirety.

The invention relates to a catalyst and catalyst layer and process for preparing dimethyl ether from synthesis gas or methanol as well as the use of the catalyst or catalyst layer in this process.

Hydrocarbons are essential in modern life and used as fuel and raw materials, including the chemical, petrochemical, plastics and rubber industry. Fossil fuels such as oil and natural gas are composed of hydrocarbons with a specific ratio of carbon to hydrogen. Despite their wide application and high demand, fossil fuels also have limitations and disadvantages in view of being a finite resource and their contribution to global warming if they are burned.

Research on alternative fuels was mainly started due to ecological and economical considerations. Among the alternative fuels, dimethyl ether (DME), which was recently discovered as a clean fuel, can be synthesized from synthetic gas which was generated from different primary sources. These primary sources can be natural gas, coal, heavy oil, and also biomass. Up to now, only two DME synthesis procedures from synthesis gas have been claimed, one of these being the traditional methanol synthesis, followed by a dehydration step, and the other being a direct conversion of synthesis gas to DME in one single step.

Recently attention has been directed towards the direct synthesis of dimethyl ether from synthesis gas, using a catalytic system that combines a methanol synthesis catalyst and a catalyst for dehydration of said alcohol. It was confirmed on the basis of experimental studies that both the stage of methanol synthesis and the stage of methanol dehydration could be conducted simultaneously on one appropriate catalytic system. Depending upon the applied synthesis gas, the catalyst might additionally show water gas shift activity.

Most known methods of producing methanol involve synthesis gas. Synthesis gas is a mixture of mainly hydrogen, carbon monoxide and carbon dioxide, from which methanol is produced over a catalyst.

$$CO + 2H_2 \leftrightarrow CH_3OH$$

In a following step methanol can be converted into DME by dehydration over an acidic catalyst.

$$2CH_3OH \leftrightarrow CH_3OCH_3 + H_2O$$

In the direct DME production there are mainly two overall reactions that occur from synthesis gas. These reactions, reaction (1) and reaction (2), are listed below.

$$3CO + 3H_2 \leftrightarrow CH_3OCH_3 + CO_2 \quad (1)$$

$$2CO + 4H_2 \leftrightarrow CH_3OCH_3 + H_2O \quad (2)$$

Reaction (1) occurs with the combination of three reactions, which are methanol synthesis reaction, methanol dehydration reaction, and water gas shift reaction:

$$2CO + 4H_2 \leftrightarrow 2CH_3OH \text{ (methanol synthesis reaction)}$$

$$2CH_3OH \leftrightarrow CH_3OCH_3 + H_2O \text{ (methanol dehydration reaction)}$$

$$CO + H_2O \leftrightarrow CO_2 + H_2 \text{ (water gas shift reaction)}$$

Reaction (1) has a stoichiometric ratio $H_2/CO$ of 1:1 and has some advantages over reaction (2). For example, reaction (1) generally allows higher single pass conversions and less energy-consuming in comparison to the removal of water from the system in reaction (2).

Methods for the preparation of dimethyl ether are well-known from prior art. Several methods are described in the literature where DME is produced directly in combination with methanol by the use of a catalyst active body in both the synthesis of methanol from synthesis gas and methanol dehydration. Suitable catalysts for the use in the synthesis gas conversion stage include conventionally employed methanol catalyst such as copper and/or zinc and/or chromium-based catalyst and methanol dehydration catalyst.

WO 2013/120938 relates to a catalytically active body for the synthesis for dimethyl ether from synthesis gas. In the introductory part of this document, several prior art references are discussed which disclose different catalysts and process options for this process.

Chemical Engineering Journal 203 (2012), pages 201 to 211, discloses activity and deactivation studies for direct dimethyl ether synthesis using Cu—ZnO—Al$_2$O$_3$ with NH$_4$ZSM-5, HZSM-5 or γ-Al$_2$O$_3$. The catalyst system is employed for the production of dimethyl ether from syngas. It was found that of the solid acids which are necessary for the dehydration function of the admixed system, the CuO—ZnO—Al$_2$O$_3$/HZSM-5 bifunctional catalyst showed highest stability over a continuous period of 212 h. This particular system was observed to lose around 16.2% of its initial activity over this operating period.

Studies Surf. Sci. Cat. 111 (1997), pages 175 to 182, discloses a slurry-phase synthesis gas-to-DME process in which both catalysts for methanol synthesis and the methanol dehydration reactions deactivate rapidly.

Natural Gas Conversion VIII, Elsevier 2007, pages 403 to 408, discloses the slurry phase DME direct synthesis technology. In FIG. 2 on page 406 the deactivation of the DME synthesis catalyst over an operation time of 0 to 350 hours is disclosed.

The references above show that the catalysts employed in the synthesis gas-to-dimethyl ether (DME) process undergo rapid deactivation.

The known processes are often not satisfying with regard to the long-term stability of the catalyst system employed or of components thereof.

The object underlying the present invention is to provide a catalyst as well as a multi-component catalyst system which has a significantly improved long-term stability in the direct synthesis of dimethyl ether from synthesis gas or methanol.

The object is achieved according to the present invention by a catalyst comprising or consisting of methanol-to-dimethyl ether catalyst particles which comprises a catalytically active component, selected from the group consisting of
(i) acidic alumosilicate, silicate, zeolite, aluminium oxide like gamma-alumina or mixtures thereof,
(ii) acidic aluminium hydroxide, aluminium oxide hydroxide, and/or γ-aluminium oxide with 0.1 to 20 weight % of niobium, tantalum, phosphorous or boron, based on the catalytically active component or mixtures thereof or (iii) acidic niobium oxide, tantalum oxide, titanium oxide, zirconium oxide, silicon oxide, aluminium phosphate, niobium phosphate, or mixtures thereof, wherein the methanol-to-dimethyl ether catalyst particles further more comprise at least one transition metal.

The object is furthermore achieved by the use of this catalyst in a synthesis gas-to-dimethyl ether process.

The object is furthermore achieved by the use of this catalyst in a catalyst layer comprising an admixture of these catalyst particles with synthesis gas-to-methanol catalyst particles.

The object is furthermore achieved by a catalyst layer comprising an admixture of these methanol-to-dimethyl ether catalyst particles and synthesis gas-to-methanol catalyst particles.

The object is furthermore achieved by the use of the catalyst or the catalyst layer in a methanol-to-dimethyl ether process.

The object is furthermore achieved by a process for preparing dimethyl ether from methanol, comprising contacting methanol with this catalyst or catalyst layer under dehydrating conditions.

It has been found that by employing a specific acidic catalyst, which furthermore comprises at least one transition metal, in a methanol-to-dimethyl ether process or synthesis gas-to-dimethyl ether process, the catalyst has a long-term stability. The catalyst deactivation can be minimized or at least significantly reduced.

The term "mixtures" can also mean "a mixture".

In the catalyst, the at least one transition metal is preferably selected from elements of the groups 8, 9, 10, 11 of the periodic table or a mixture thereof.

The amount of the at least one transition metal is preferably 0.01 to 20 weight %, more preferably 0.1 to 15 weight %, specifically 0.3 to 5 weight %, for example 0.5 weight %, based on the total weight of the methanol-to-dimethyl ether catalyst particles.

Most preferred is Cu, which is most preferably employed in an amount of from 0.3 to 2 weight %, based on the total weight of the methanol-to-dimethyl ether catalyst particles.

The methanol-to-dimethyl ether catalyst particles can furthermore comprise an inorganic oxide binder material which is different from the catalytically active component.

This inorganic oxide binder material is preferably selected from the group consisting of $Al_2O_3$, $SiO_2$, $TiO_2$, $ZrO_2$, or mixtures thereof.

The amount of the inorganic oxide binder material is preferably 10 to 90 weight %, more preferably 20 to 70 weight %, specifically 30 to 50 weight %, for example 40 weight %, based on the total weight of the methanol-to-dimethyl ether catalyst particles.

The total amount of the ingredients or components of the methanol-to-dimethyl ether-catalyst particles always adds up to 100 weight %. Thus, if for example 20 weight % of the transition metal are employed, the amount of the inorganic oxide binder material must be below 80 weight % to allow for the presence of the catalytically active component.

Preferably, the methanol-to-dimethyl ether catalyst particles are formed of an acidic alumosilicate zeolite with a $SiO_2$:$Al_2O_3$ molar ratio of from 10 to 1500:1, preferably 50 to 1200:1, more preferably 200 to 1000:1, for example 280:1, 400:1 or 900:1, comprising 10 to 90 weight % of at least one binder material and 0.01 to 20 weight % of the at least one transition metal, based on the total weight of the methanol-to-dimethyl ether catalyst particles, which is 100 weight %.

Most preferably, the methanol-to-dimethyl ether catalyst particles are formed of 30 to 80 weight % of at least one acidic alumosilicate of framework type MFI, 20 to 70 weight % of at least one binder material selected from $Al_2O_3$, $SiO_2$, $TiO_2$ and $ZrO_2$, and 0.1 to 5 weight % of elements of the groups 8, 9, 10, 11 of the periodic table or a mixture thereof, based on the total weight of the methanol-to-dimethyl ether catalyst particles, which is 100 weight %.

The catalyst comprises or consists of the methanol-to-dimethyl ether catalyst particles. Thus, the catalyst can contain further components besides the methanol-to-dimethyl ether catalyst particles. Preferably, the catalyst consists of the methanol-to-dimethyl ether catalyst particles.

The catalyst or the methanol-to-dimethyl ether catalyst particles are employed in a catalyst layer comprising an admixture of these with synthesis gas-to-methanol catalyst particles.

This catalyst layer can itself be part of a catalyst system comprising two catalyst layers 1 and 2, wherein the above-mentioned catalyst layer forms the catalyst layer 2.

In the following, the catalyst layer according to the present invention is further illustrated as catalyst layer 2 in connection with catalyst layer 1. All features described below for catalyst layer 2 also relate to the above-mentioned catalyst layer.

The catalyst system for a continuous synthesis gas-to-dimethyl ether process comprises two spatially separated subsequent catalyst layers 1 and 2 in flow direction, catalyst layer 1 comprising synthesis gas-to-methanol catalyst particles, catalyst layer 2 comprising an admixture of synthesis gas-to-methanol catalyst particles and methanol-to-dimethyl ether catalyst particles.

The admixture of the two different catalyst particles in catalyst layer 2 is preferably a physical mixture of two different sets of individual catalyst particles and the admixture can also comprise one set of catalyst particles each consisting of synthesis-gas-to-methanol catalyst and methanol-to-dimethyl ether catalyst.

This catalyst system as defined above is used for producing dimethyl ether from synthesis gas.

The corresponding process for preparing dimethyl ether from synthesis gas comprises administering synthesis gas to the inlet to catalyst layer 1 in a catalyst system as defined above and removing dimethyl ether-containing product gas from the outlet of catalyst layer 2.

It has been found that by employing the catalyst or catalyst layer in a specific sequence of two separate subsequent catalyst layers in a catalyst system, preferably a tubular reactor, the catalyst deactivation can be minimized or at least significantly reduced.

In this process two catalysts are employed, i.e. a methanol synthesis catalyst and a methanol dehydration catalyst. The methanol synthesis catalyst can also be described as the synthesis gas-to-methanol catalyst. This catalyst catalyses the chemical reaction starting from synthesis gas and leading to methanol. Thus, when employing this catalyst, methanol is the main product when starting the reaction from synthesis gas. Other products are only formed to a minor extent.

The methanol dehydration catalyst can also be described as methanol-to-dimethyl ether catalyst. This catalyst catalyses the reaction starting from methanol and leading to dimethyl ether and water. Dimethyl ether and water are the main products and other products are only formed to a minor extent.

Both catalysts preferably catalyse side reactions not leading to the described main product only to minor extents, e.g. less than 20%.

The term "catalyst layer" defines a close spatial relationship of individual catalyst particles. Thus, the catalyst particles and the catalyst layers can be in direct contact with each other or in a close spatial relationship in which they are not in direct contact with each other. For example, the catalyst layers can be present as packed beds or slurries. Thus, the term "catalyst layer" is not restricted to fixed or packed beds but also encompasses situations in which individual catalyst particles are separated, e.g. by fluids.

The catalyst system can be freely chosen as long as it allows for a continuous process and for spatially separating the two subsequent catalyst layers 1 and 2.

The catalyst system is employed in one or more containments, which allow for the special separation of the subsequent catalyst layers 1 and 2. Thus, the containment has at least two sections in which the catalyst layers 1 and 2 are located, and the two sections are linked in a way that the reactants can flow from catalyst layer 1 to catalyst layer 2.

Depending on the type of catalyst layers, the catalyst system may be employed in one or more tubular reactors or in two or more tank reactors. It is also possible to employ a series of at least two loop reactors in which the respective catalyst slurries are moved in a loop. Combinations of the different catalyst systems can also be employed. The construction of the catalyst system is not further limited, as long as it allows spatial separation of the two catalyst layers 1 and 2 and their subsequent arrangement so that the reactants flow from the catalyst layer 1 to catalyst layer 2.

Typically, no methanol is isolated between catalyst layers 1 and 2. This means that typically the reaction product coming from catalyst layer 1 is directly fed to catalyst layer 2 without being further purified, concentrated or submitted to any other work-up sequence.

The catalyst layers 1 and 2 can be separated, for example by some length of tubing, by inert particle beds or other means.

The synthesis gas-to-methanol catalyst particles can be chosen from all catalyst particles that catalyse this reaction. Preferably, the catalyst particles comprise copper oxide, aluminium oxide, zinc oxide, zirconium oxide, amorphous aluminium oxide, ternary oxide or mixtures thereof, or comprise PdZn or comprise $Cr_2O_3/ZnO$. These catalyst systems are described, for example, in WO 2013/160133, WO 2013/120945 and WO 2013/120938, respectively.

The catalyst layer 2 preferably comprises a mixture of
(A) 60 to 80 weight % of synthesis gas-to-methanol catalyst particles, comprising a catalytically active component, selected from the group consisting of copper oxide, aluminium oxide, zinc oxide, zirconium oxide, amorphous aluminium oxide, ternary oxide or mixtures thereof,
(B) 20 to 40 weight % of methanol-to-dimethyl ether catalyst particles, comprising a catalytically active component, selected from the group consisting of
  (i) acidic alumosilicate, silicate, zeolite, aluminium oxide like gamma-alumina or mixtures thereof;
  (ii) acidic aluminium hydroxide, aluminium oxide hydroxide, and/or gamma-aluminium oxide with 0.1 to 20 weight % of niobium, tantalum, phosphorous or boron, based on the catalytically active component (B) or mixtures thereof or
  (iii) acidic niobium oxide, tantalum oxide, titanium oxide, zirconium oxide, silicon oxide, aluminium phosphate, niobium phosphate, or a mixture thereof,
(C) 0 to 10 weight % of at least one additive.

Suitable catalyst layer 2 particles are described in WO 2013/160133, WO 2013/120945 and WO 2013/120938, respectively.

Preferably, the synthesis gas-to-methanol catalyst particles in catalyst layers 1 and 2 are the same.

Catalyst layer 1 comprises the synthesis gas-to-methanol catalyst particles preferably as the only catalytically active particles. In other words, catalyst layer 1 preferably does not contain methanol-to-dimethyl ether catalyst particles.

Both catalyst layers 1 and 2 can comprise inert particles for diluting the catalyst particles. The term "inert particles" defines a particulate catalytically inactive material.

Typically, catalyst systems employed as slurries do not contain inert materials/catalytically inactive materials.

Specifically, the synthesis gas-to-methanol particles in catalyst layer 1 are in admixture with inert 1 particles. These inert 1 particles can be freely chosen as long as they do not interfere in the chemical reaction starting from synthesis gas and leading to methanol. The inert 1 particles are preferably selected from the group consisting of $Al_2O_3$, glass beads, SiC, steatite or mixtures thereof.

The catalyst system for a continuous synthesis gas-to-dimethyl ether process as outlined above preferably comprises two separate subsequent catalyst layers 1 and 2 in flow direction, the catalyst layers 1 and 2 having a volume ratio of from 9:1 to 1:9, catalyst layer 1 being formed of a packed bed of catalyst 1 particles or an admixture of catalyst 1 particles and inert 1 particles in a weight ratio of from 1:4 to 4:1, catalyst 1 comprising 5 to 80 weight % CuO, besides ZnO, $Al_2O_3$ and optionally $ZrO_2$, inert 1 particles comprising $Al_2O_3$, catalyst layer 2 being formed of a packed bed of an admixture of catalyst 1 particles and catalyst 2 particles in a weight ratio of from 1:9 to 9:1, catalyst 2 particles being formed of an acidic alumosilicate zeolite with a $SiO_2:Al_2O_3$ molar ratio of from 10 to 1500:1, comprising 10 to 90 weight % of at least one binder material and 0.01 to 20 weight % of the at least one transition metal, based on the total weight of catalyst 2 particles, which is 100 weight %.

In the following the catalyst system which can be located in one or more tubular reactors is described as a tubular reactor, which is a preferred embodiment.

In a first layer 1, a packed bed of a methanol synthesis catalyst in admixture with inert 1 particles is employed. In the second, subsequent downstream catalyst layer 2 a mixture of the methanol synthesis catalyst and a methanol dehydration catalyst is employed.

It was found, by employing specific ratios of the two catalyst beds and specific ratios of the two components in each catalyst bed in combination with a specific methanol synthesis catalyst and methanol dehydration catalyst, the deactivation of the catalyst can be minimized most effectively.

Furthermore it was found, by employing the tubular reactor comprising the two separate subsequent catalyst layers 1 and 2, the maximum temperature to which the catalyst is exposed during the dimethyl ether synthesis process can be limited. Preferably, the temperature in catalyst layers 1 and 2 is kept within the range of from 200 to 400° C., more preferably 220 to 360° C., even more preferably 240 to 320° C.

Preferably, the maximum temperature in the catalyst layers 1 and 2 in the tubular reactor should be limited to 320° C. or lower, more preferably 290° C. or lower, specifically 280° C. or lower.

Furthermore, in catalyst layer 1 the minimum temperature should be preferably 240° C. or higher, more preferably 250° C. or higher, specifically 260° C. or higher.

In catalyst layer 2, the minimum temperature should be preferably 240° C. or higher, more preferably 260° C. or higher, specifically 270° C. or higher.

This leads to a preferred temperature range in catalyst layer 1 of from 240 to 320° C., more preferably 250 to 290° C., specifically 260 to 280° C.

In catalyst layer 2, the temperature range is preferably 240 to 320° C., more preferably 260 to 290° C., specifically 270 to 280° C.

Consequently, a temperature control in the catalyst layers 1 and 2 to maintain a catalyst bed temperature in the above ranges is advantageous for minimizing the catalyst deactivation.

The synthesis gas-to-dimethyl ether (DME) process or methanol-to-dimethyl ether process is according to the present invention preferably carried out in a tubular reactor through which the synthesis gas flows and which contains the two separate catalyst layers. In flow direction of the synthesis gas, first catalyst layer 1 is passed and then catalyst layer 2. Both catalyst layers are preferably packed beds which are separate from one another, i.e. they are not mixed but spatially separated. The separation can be achieved by an interlayer of inert particles spatially separating the two catalyst layers. However, it is also possible that catalyst layer 2 directly follows catalyst layer 1, so that both catalyst layers are adjacent.

Synthesis gas, or briefly syngas, is a mixture of carbon monoxide, carbon dioxide and hydrogen. Syngas can be produced from many sources, including natural gas, coal, biomass or virtually any hydrocarbon feed store, by reaction with steam or oxygen. The formation of syngas is strongly endothermic and requires high temperatures. Steam reforming of natural gas or shale gas is typically performed in tubular reactors that are heated externally. The process typically employs nickel catalysts on a special support that is resistant against the harsh process conditions. Typically syngas with $H_2/CO$ ratios in the range of 3 to 4 is obtained in this manner.

Alternative routes to syngas are the partial oxidation of methane or other hydrocarbons yielding syngas with a $H_2/CO$ ratio of about 2.

Autothermal reforming is a hybrid which combines methane steam reforming and oxidation in one process. These and alternative routes to syngas are disclosed in J. van de Loosdrecht and J. W. Niemantsverdriet, "Chemical energy storage", R. Schlögl, Ed., De Gruyter, Berlin, 2013, Chapter "Synthesis gas to hydrogen, methanol, and synthetic fuels".

According to the present invention, syngas with $H_2/CO$ ratios in the range of from 1 to 10, preferably from 1 to 3 can be employed, or a stoichiometric number of 0.7 to 2.2.

The process according to the present invention starts from methanol and leads to dimethyl ether as the desired product. The process as such is as discussed above.

The tubular reactor preferably employed according to the present invention is an elongated tube which has a diameter which is much smaller than the length of the tube. A typical tube can have a circular or ellipsoidal cross-section. Preferably, the cross-section is circular, having a diameter of preferably 1 to 5 cm, more preferably 2 to 3 cm.

The tubular reactor is preferably equipped with an external heating. Preferably, the tubular reactor possesses at least two independent heating sections for independent heating of catalyst layers 1 and 2.

Catalyst layers 1 and 2 are employed in the tubular reactor preferably in a volume ratio of from 9:1 to 1:9, preferably 1:1.5 to 1:3, more preferably 1:1.8 to 1:2.5, most preferably 1:2 to 3:4.

Typically, the volume of catalyst layer 2 is higher than the volume of catalyst layer 1 if catalyst layer 1 contains 50 weight % of inert 1 particles.

Depending on the inner diameter of the tubular reactor, the percentage of inert 1 particles in catalyst layer 1 can be modified. Higher diameters of above 3 cm might require amounts of more than 50 weight % inert 1 particles in catalyst layer 1 in order to achieve an adequate temperature control.

Catalyst layer 1 is preferably a packed bed of an admixture of catalyst 1 particles and inert 1 particles in a weight ratio of from 1:4 to 4:1, preferably 3:7 to 7:3, more preferably 2:3 to 3:2, for example around 1:1.

The admixture typically means that catalyst 1 particles and inert 1 particles are separately provided and then admixed so that they form a physical particle mixture.

Catalyst 1 is a methanol formation catalyst and preferably comprises 5 to 80 weight % CuO besides ZnO, $Al_2O_3$ and optionally $ZrO_2$. The amount of CuO, based on catalyst 1 particles, is 5 to 80 weight %, more preferably 30 to 70 weight %, particularly 50 to 70 weight %, especially 55 to 65 weight %, for example 60 weight %.

The remainder of catalyst 1 particles, ZnO, $Al_2O_3$ and optionally $ZrO_2$, are typically employed in a constant weight ratio. Based on the total weight of the catalyst 1 particle (all ingredients sum up to 100 weight %), the amount of ZnO is preferably 10 to 30 weight %, more preferably 15 to 25 weight %, specifically 18 to 21 weight %. The amount of $Al_2O_3$ is preferably 10 to 30 weight %, more preferably 12 to 22 weight %, more preferably 16 to 18 weight %. The amount of $ZrO_2$, if present, is preferably in the range of from 0.5 to 5 weight %, more preferably 1 to 4 weight %, specifically 2 to 3 weight %.

Preferably, catalyst 1 particles comprise, based on the total weight of catalyst 1 particles, which is 100 weight %, 30 to 70 weight % CuO, 10 to 30 weight % ZnO, 10 to 30 weight % $Al_2O_3$, 1 to 5 weight % $ZrO_2$, and 0 to 7 weight % of further additives, e.g. 1 to 7 weight % of a solid tableting lubricant. Further additives may be the additives typically employed in the production of catalyst particles. Reference can be made to WO 2013/120938, page 7, lines 33 ff. Other additives are disclosed in this reference as well.

Typical catalysts and inert particles employed in a slurry process have a more or less spherical shape or a particulate form that is not especially critical. When catalyst layers 1 and 2 are present as slurries, the average particle size $d_{50}$ is preferably from 50 to 500 μm. The particle size is measured with an optical particle sizer.

If packed beds are employed, typical catalyst 1 particles as well as inert 1 particles and catalyst 2 particles are extrudates with an average maximum diameter of from 1 to 3.5 mm and a ratio of average length to average maximum diameter of from 0.5:1 to 10:1.

The term "average maximum diameter" is typically measured by measuring the maximum diameter of a number of extrudates (typically 10 extrudates) and deriving the average of this diameter. For a circular cross-section, there is only one diameter of the extrudates. For a noncircular cross-section, e.g. an ellipsoidal cross-section, the maximum diameter is measured and the average over ten samples is taken.

The average length is measured in a similar manner and obtained from measuring ten extrudate samples.

Preferably, the extrudates of catalyst 1 particles, catalyst 2 particles and inert 1 particles have an average maximum diameter of from 0.5 to 5 mm, more preferably 1 to 3.5 mm, specifically 1.3 to 2.0 mm. Examples of useful diameters are 1.5 to 1.6 mm and 3 to 3.2 mm.

The ratio of average length to average maximum diameter is preferably 0.5:1 to 10:1, more preferably 1:1 to 3:1, specifically 1:1 to 2:1.

The catalyst 1 particles can be prepared as described below or as described in EP-A 1 238 701, WO 2013/120938 and WO 2013/120945 and the documents cited therein.

The inert 1 particles preferably comprise $Al_2O_3$. Thus, the inert 1 particles can be $Al_2O_3$ alone or a mixture of $Al_2O_3$ particles with other inert particles.

Since $Al_2O_3$ is present in catalyst 1 particles as well, the overall content of $Al_2O_3$ in catalyst layer 1 can be adjusted by adjusting the amounts of $Al_2O_3$ in catalyst 1 particles and inert 1 particles, respectively.

The catalyst layer 2, which follows catalyst layer 1, is preferably a packed bed of an admixture of catalyst 1 particles and catalyst 2 particles in a weight ratio of from 1:9 to 9:1, preferably 6.5:3.5 to 8.5:1.5, specifically 3:2 to 7:3.

The catalyst 1 particles employed in catalyst layers 1 and 2 can be the same.

The catalyst 2 particles are formed of an acidic alumosilicate zeolite with a $SiO_2:Al_2O_3$ molar ratio of from 10 to 1500:1, preferably 50 to 1200:1, more preferably 200 to 1000:1, for example 280:1, 400:1 or 900:1.

Typical acidic zeolites can be chabazite, mordenite, γ-zeolite, β-zeolite, Usy or of the framework type MFI. Preferably, the acidic zeolite is of framework type MFI, specifically ZSM-5.

The catalyst 2 particles comprise 10 to 90 weight %, more preferably 20 to 70 weight %, specifically 30 to 50 weight %, for example 40 weight % of at least one binder material, based on the total weight of catalyst 2 particles. Optionally, a transition metal like Cu can be present.

According to the invention, 0.01 to 20 weight %, preferably 0.1 to 15 weight %, specifically 0.3 to 5 weight %, for example 0.5 weight %, based on the total weight of the catalyst particles, which is 100 weight %, of a transition metal are employed, which is preferably selected from elements of the groups 8, 9, 10, 11 of the periodic table or a mixture thereof, most preferably Cu.

Preferably, the at least one binder material is selected from $Al_2O_3$, $SiO_2$, $TiO_2$ and $ZrO_2$. Most preferably, $Al_2O_3$ is employed as the binder material. The sum of the ingredients of catalyst 2 particles adds up to 100 weight %.

Most preferred are catalyst 2 particles which comprise ZSM-5 alumosilicate, $Al_2O_3$ as binder material and copper.

The catalyst 2 particles can be produced as described below or according to processes similar to those disclosed for producing catalyst 1 particles.

The catalyst 2 particles are typically prepared by intimately mixing powders of the acidic zeolite and the binder material which is used in the form of the corresponding oxide, hydroxide, oxide hydroxide materials, and, if needed a peptizing agent like organic or inorganic acids, e.g. $HNO_3$, formic acid or acetic acid, and an organic pore-forming material, like carboxymethyl cellulose.

To the powder mixture a necessary amount of liquid is added so that a material is obtained which can be kneaded. The material is subsequently pressed through an orifice, so that extrudates are obtained.

The metal dopant, preferably copper, can be admixed with the powders before kneading, or extrudates can be impregnated with a solution of a soluble salt or complex of the metal.

Drying and calcining can be performed in a known manner.

The tubular reactor comprises the two separate and subsequent catalyst layers 1 and 2 in one or more tubular reactors. Further layers of catalyst materials or inert materials can be provided if considered necessary. According to the preferred embodiment, only catalyst layers 1 and 2 as defined above are present as catalysts in the tubular reactor. It is, furthermore, possible to employ an additional guard bed or additional layers of inert material.

The catalyst system, preferably the tubular reactor is employed in a process for preparing dimethyl ether from synthesis gas. In this process, synthesis gas is administered to the inlet to catalyst layer 1. Dimethyl ether-containing product gas is removed from the outlet of catalyst layer 2. Preferably, the temperature in the catalyst layers 1 and 2 is kept within the range as indicated above.

When running the process according to the present invention, the synthesis gas is preferably preheated and the catalyst layers 1 and 2 are preheated and the desired catalyst bed temperature is monitored and controlled separately for both catalyst beds. If necessary, the synthesis gas can be diluted by an inert gas in order to achieve the desired temperature profile.

The present invention is further illustrated by the examples below.

EXAMPLES

The tubular reactor (inner diameter of 1", total length of 2 meters) possesses two independent heating sections: heating section one from 0 to 0.8 meters, heating section two from 0.8 to 2 meters of the reactor length. Each section can be heated to a different temperature.

The two catalyst layers are filled in such a way that the catalyst layer one is located within the heating section one and the catalyst layer two is located within the heating section two. The catalyst layer one has a weight of 270 g, a volume of 330 ml and a height of 0.6 m. The catalyst layer two has a weight of 430 g, a volume of 450 ml and a height of 0.95 m.

Catalyst Layer 1

The first catalyst layer comprises a 50:50 weight % mixture of synthesis-gas-to-methanol catalyst and an inert material alpha alumina oxide. The synthesis-gas-to-methanol catalyst contains 58.3 weight % CuO, 19.4 weight % ZnO, 17.0 weight % $Al_2O_3$, 2.4 weight % $ZrO_2$ and 2.9 weight % graphite as lubricant for tableting to cylindrical shaped bodies with diameter and height of 3 mm.

The synthesis-gas-to-methanol catalyst is prepared in the following way: A solution of copper, aluminium, zinc and zirconium salts, the atomic Cu:Al:Zn:Zr ratio being 1:0.5:0.3:0.03, is precipitated with a sodium hydroxide and carbonate solution at a pH of 9 and at from 25 to 50° C. The precipitate is filtered off the suspension and washed with deionized water until the washing water is free of nitrates. The precipitate is dried. The dried precipitate is calcined at from 250 to 800° C. to give a mixed oxide. The calcined material is mixed with 3 weight % graphite powder. The mixture is formed to cylindrical tablets with a diameter and height of 3 mm.

Catalyst Layer 2

The second catalyst layer comprises an 70%:30% or 60%:40% weight %-mixture of synthesis-gas-to-methanol catalyst just described and of methanol-to-dimethyl ether catalyst. The methanol-to-dimethyl ether catalyst contains 60 weight % ZSM-5 zeolite as acidic component and 40 weight % alumina oxide as binder for extrusion to cylindrical shaped bodies with diameter of 3.2 mm or 1.6 mm and a length of up to 3.2 mm. In addition, the cylindrical shaped bodies containing zeolite and alumina oxide can be impregnated with 0.5 weight % copper.

The methanol-to-dimethyl ether catalyst is prepared in the following way: Powder of ZSM-5 zeolite is mixed together with aluminium oxide hydroxide, the weight ratio being 1.5:1. Formic acid, carboxy methyl cellulose and water is added in necessary amount to obtain material that can be kneaded. After kneading the material is pressed through an extruder die. The extruded material is dried and afterwards calcined at from 400 to 700° C. In addition, the calcined material can be further impregnated with copper. Therefore, a copper salt solution is contacted with the extruded material in necessary amount to obtain extrudates with 0.5 weight-% copper. The copper loaded material is dried and then calcined at from 200 to 350° C.

The described catalytic materials are used in the process for dimethyl ether synthesis from synthesis gas. It was found that the catalyst activity, demonstrated by conversion of synthesis gas, is less reduced over time if a DME synthesis catalyst with copper impregnation is used compared to a DME synthesis catalyst without copper.

The described catalytic materials are used in the process for dimethyl ether synthesis from synthesis gas.

Comparative Example 1

The reactor is filled with 947 ml of a 60%:40% weight-%-mixture of synthesis-gas-to-methanol catalyst and of methanol-to-dimethyl ether catalyst. The synthesis-gas-to-methanol catalyst contains 58.3 weight % CuO, 19.4 weight % ZnO, 17.0 weight % $Al_2O_3$, 2.4 weight % $ZrO_2$ and 2.9 weight % graphite as lubricant for tableting to cylindrical shaped bodies with diameter and height of 3 mm. The dimethyl ether synthesis catalyst contains 60 weight % ZSM-5 zeolite as acidic component and 40 weight % alumina oxide as binder for extrusion to cylindrical shaped bodies with diameter of 3.2 mm and a length of up to 3.2 mm.

The catalyst bed is activated with hydrogen using commonly known activation procedures. Then, a flow of 4550 NL/h of synthesis gas which comprises 62 vol % $H_2$, 23 vol % CO, 5 vol % $CO_2$ and 10 vol % Ar is applied to the catalyst bed at 70 bar. Before entering the reactor with the catalyst bed the synthesis gas is preheated to 255° C. The heating section one of the reactor is heated to 255° C. and the heating section two of the reactor is heated to 270° C. The catalyst converts the synthesis gas to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

Example 2

The reactor is filled with 692 ml of a 50%:50% weight-%-mixture of synthesis-gas-to-methanol catalyst and of methanol-to-dimethyl ether catalyst. The synthesis-gas-to-methanol catalyst contains 58.3 weight % CuO, 19.4 weight % ZnO, 17.0 weight % $Al_2O_3$, 2.4 weight % $ZrO_2$ and 2.9 weight % graphite as lubricant for tableting to cylindrical shaped bodies with diameter and height of 3 mm. The methanol-to-dimethyl ether catalyst contains 60 weight % ZSM-5 zeolite as acidic component and 40 weight % alumina oxide as binder for extrusion to cylindrical shaped bodies with diameter of 1.6 mm and a length of up to 3.2 mm. In addition, the cylindrical shaped bodies containing zeolite and alumina oxide are impregnated with 0.5 weight % copper.

The catalyst bed is activated with hydrogen using commonly known activation procedures. Then, a flow of 1326 NL/h of synthesis gas which comprises 62 vol % $H_2$, 23 vol % CO, 5 vol % $CO_2$ and 10 vol % Ar is applied to the catalyst bed at 50 bar. Before entering the reactor with the catalyst bed the synthesis gas is preheated to 259° C. The heating section one of the reactor is heated to 259° C. and the heating section two of the reactor is heated to 273° C. The catalyst converts the synthesis gas to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

It was found that the catalyst activity, demonstrated by conversion of synthesis gas, is less reduced over time if the dimethyl ether synthesis catalyst is impregnated with 0.5 weight-% copper (example 2) compared to the copper-free dimethyl ether synthesis catalyst (comparative example 1).

Example 3

The reactor is filled with two catalyst layers. The catalyst layer one, which is located at the reactor inlet within the heating section one, comprises 330 ml of a 50%:50% weight-%-mixture of synthesis-gas-to-methanol catalyst and of an inert material alpha alumina oxide. The synthesis-gas-to-methanol catalyst contains 58.3% weight % CuO, 19.4 weight % ZnO, 17.0 weight % $Al_2O_3$, 2.4 weight % $ZrO_2$ and 2.9 weight % graphite as lubricant for tableting to cylindrical shaped bodies with diameter and height of 3 mm.

The catalyst layer two, which is located directly behind the catalyst layer one within the heating section two, comprises 450 ml of an 700%:30% weight-%-mixture of synthesis-gas-to-methanol catalyst just described and of methanol-to-dimethyl ether catalyst. The methanol-to-dimethyl ether catalyst contains 60 weight % ZSM-5 zeolite as acidic component and 40 weight % alumina oxide as binder for extrusion to cylindrical shaped bodies with diameter of 1.6 mm and a length of up to 3.2 mm. In addition, the cylindrical shaped bodies containing zeolite and alumina oxide are impregnated with 0.5 weight % copper.

The catalyst bed is activated with hydrogen using commonly known activation procedures. Then, a flow of 2152 NL/h of synthesis gas which comprises 62 vol % $H_2$, 23 vol % CO, 5 vol % $CO_2$ and 10 vol % Ar is applied to the catalyst bed at 50 bar. Before entering the reactor with the catalyst bed the synthesis gas is preheated to 256° C. Also the heating section one of the reactor with the catalyst layer one inside is heated to 256° C. The heating section two of the reactor with the catalyst layer two inside is heated to 260° C. The catalyst layer one partially converts the synthesis gas to methanol. The resulting gas, comprising methanol and unconverted synthesis gas, is subsequently directed to the catalyst layer two where the synthesis gas/methanol mixture is further converted to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

It was found that the catalyst activity, demonstrated by conversion of synthesis gas, is even less reduced over time if the methanol-to-dimethyl ether synthesis catalyst is impregnated with 0.5 weight-% copper and if the catalyst bed in the reactor comprises a two layer composition (example 3) instead of one catalyst layer (comparative example 1).

The catalyst deactivation in examples 1 to 3 was determined by measuring the relative catalyst activity in dependence on the time-on-stream in a range of from 25 to 400 hours. The relative catalyst activity was determined from the product gas composition. The following deactivation in %/h was obtained.

Example 1: 0.04
Example 2: 0.006
Example 3: 0.001.

The temperature in the catalyst bed in the heating section 2 was 265 to 282° C. in example 1, 271 to 277° C. in example 2 and 270 to 275° C. in example 3.

The invention claimed is:

1. A catalyst admixture of catalyst 2 particles comprising an acidic aluminosilicate zeolite with an $SiO_2:Al_2O_3$ molar ratio of from 10 to 1500:1, 10 to 90 weight % of at least one binder material and 0.01 to 20 weight % of copper, based on the total weight of catalyst 2 particles, which is 100 weight %, and catalyst 1 particles comprising 5 to 80 weight % CuO, ZnO, $Al_2O_3$ and optionally $ZrO_2$.

2. The catalyst admixture according to claim 1, formed of a packed bed of an admixture of the catalyst 1 particles and the catalyst 2 particles in a weight ratio of from 1:9 to 9:1.

3. The catalyst admixture according to claim 1, wherein in the catalyst 2 particles the amount of copper is 0.3 to 5 weight %, based on the total weight of the catalyst 2 particles.

4. The catalyst admixture according to claim 1, wherein, in the catalyst 2 particles, the binder material is an inorganic oxide binder material different from the aluminosilicate zeolite and copper.

5. The catalyst admixture according to claim 4, wherein the inorganic oxide binder material is selected from the group consisting of $Al_2O_3$, $SiO_2$, $TiO_2$, $ZrO_2$, or mixtures thereof.

6. The catalyst according to claim 4, wherein the amount of the inorganic oxide binder material is 20 to 70 weight %, based on the total weight of the catalyst 2 particles.

7. The catalyst admixture according to claim 1, wherein the catalyst 2 particles are formed of 30 to 80 weight % of at least one acidic aluminosilicate of framework type MFI, 20 to 70 weight % of at least one binder material selected from $Al_2O_3$, $SiO_2$, $TiO_2$ and $ZrO_2$, and 0.1 to 5 weight % of copper, based on the total weight of the catalyst 2 particles, which is 100 weight %.

8. The catalyst admixture according to claim 1, wherein the catalyst 2 particles comprise ZSM-5 aluminosilicate, $Al_2O_3$ as binder material, and copper.

9. The catalyst admixture according to claim 1, wherein the catalyst 1 and catalyst 2 particles have an average maximum particle diameter of from 0.5 to 5 mm.

10. A process for preparing dimethyl ether from methanol, comprising contacting methanol with the catalyst admixture according to claim 1 under dehydrating conditions.

11. The process according to claim 10, wherein the temperature is in the range of from 200 to 400° C.

12. The process according to claim 10, wherein the temperature is in the range of from 270 to 280° C.

13. A synthesis gas-to-dimethyl ether process comprising contacting synthesis gas with the catalyst admixture according to claim 1.

14. The catalyst admixture according to claim 9, wherein the catalyst 1 and catalyst 2 particles are present as a packed bed of extrudates with an average maximum diameter of from 1 to 3.5 mm and a ratio of average length to average maximum diameter of from 0.5:1 to 10:1.

* * * * *